United States Patent
Varga et al.

(10) Patent No.: US 9,539,407 B2
(45) Date of Patent: Jan. 10, 2017

(54) ADJUSTABLE NEBULIZER DISPENSER

(71) Applicant: CareFusion 303, Inc., San Diego, CA (US)

(72) Inventors: Christopher Varga, Laguna Hills, CA (US); Thomas Dillingham, Aliso Viejo, CA (US); Brian Pierro, Yorba Linda, CA (US); Khalid Mansour, Corona, CA (US)

(73) Assignee: VYAIRE MEDICAL CONSUMABLES LLC, Yorba Linda, CA (US)

( * ) Notice: Subject to any disclaimer, the term of this patent is extended or adjusted under 35 U.S.C. 154(b) by 436 days.

(21) Appl. No.: 13/720,877

(22) Filed: Dec. 19, 2012

(65) Prior Publication Data
US 2014/0166010 A1    Jun. 19, 2014

(51) Int. Cl.
| | |
|---|---|
| *A61M 16/14* | (2006.01) |
| *A61M 16/04* | (2006.01) |
| *A61M 16/06* | (2006.01) |
| *A61M 16/00* | (2006.01) |
| *A61M 11/06* | (2006.01) |
| *A61M 16/08* | (2006.01) |
| *A61M 39/10* | (2006.01) |

(52) U.S. Cl.
CPC .............. *A61M 16/14* (2013.01); *A61M 11/06* (2013.01); *A61M 16/049* (2014.02); *A61M 16/0825* (2014.02); *A61M 16/0833* (2014.02); *A61M 16/06* (2013.01); *A61M 16/0666* (2013.01); *A61M 16/0875* (2013.01); *A61M 39/1055* (2013.01)

(58) Field of Classification Search
None
See application file for complete search history.

(56) References Cited

U.S. PATENT DOCUMENTS

| | | | |
|---|---|---|---|
| 1,950,577 A * | 3/1934 | Stephenson | A61M 11/041 128/200.11 |
| 5,027,809 A | 7/1991 | Robinson | |
| 5,286,071 A * | 2/1994 | Storage | F16L 27/04 285/226 |
| 5,357,945 A | 10/1994 | Messina | |
| 5,921,239 A * | 7/1999 | McCall | A61M 16/06 128/205.25 |

(Continued)

FOREIGN PATENT DOCUMENTS

| | | | |
|---|---|---|---|
| GB | WO 2005028011 A2 * | 3/2005 | ............... A61D 7/04 |
| WO | 2009047763 A1 | 4/2009 | |
| WO | 2012085600 A1 | 6/2012 | |

OTHER PUBLICATIONS

International Search Report and Written Opinion dated Mar. 28, 2014, for International Application No. PCT/US2013/074434.

*Primary Examiner* — Tan-Uyen (Jackie) T Ho
*Assistant Examiner* — Joseph D Boecker
(74) *Attorney, Agent, or Firm* — McDermott Will & Emery LLP

(57) ABSTRACT

A nebulizer dispenser has a T-piece, a body sealingly coupled to the T-piece and configured to contain a liquid medication, and a breathing piece sealingly coupled to the T-piece. The dispenser also has a ball-and-socket joint coupled between the T-piece and either the breathing piece or the body. The ball-and-socket joint allows relative rotational motion of the T-piece in a pitch axis, a yaw axis, and a roll axis.

20 Claims, 9 Drawing Sheets

(56) References Cited

U.S. PATENT DOCUMENTS

| | | | |
|---|---|---|---|
| 6,804,656 B1 | 10/2004 | Rosenfeld et al. | |
| 7,207,945 B2 | 4/2007 | Bardy | |
| 7,827,987 B2 * | 11/2010 | Woodard | A61M 16/06 128/204.18 |
| 7,959,574 B2 | 6/2011 | Bardy | |
| 8,042,536 B1 | 10/2011 | Howey | |
| 2005/0076913 A1 * | 4/2005 | Ho | A61M 16/06 128/206.27 |
| 2007/0004243 A1 * | 1/2007 | Ferguson-Pell | A47C 23/002 439/71 |
| 2007/0272169 A1 | 11/2007 | Barney et al. | |
| 2008/0140054 A1 | 6/2008 | Lee | |
| 2010/0231061 A1 * | 9/2010 | Van Der Walt | F16M 11/14 310/28 |
| 2011/0230820 A1 | 9/2011 | Lillis et al. | |

* cited by examiner

ADJUSTABLE NEBULIZER DISPENSER

CROSS-REFERENCE TO RELATED APPLICATIONS

Not applicable

BACKGROUND

Field

The present disclosure generally relates to nebulizers and, in particular, nebulizer dispensers that allow for adjustment of the position of the breathing piece relative to the body of the dispenser.

Description of the Related Art

Medications for certain respiratory conditions, such as asthma and chronic obstructive pulmonary disease (COPD), are often administered as an inhaled aerosol to improve delivery of the medication to the lungs. A nebulizer, also referred to as a "nebuliser," is a medical device which uses mechanical energy to transform a liquid medication into an aerosol. A nebulizer may use compressed air forced through a nozzle to break up the liquid medication into tiny globules or may use ultrasonic or vibrating-mesh mechanisms to mechanically generate the tiny globules of liquid medication.

Figure 1A:
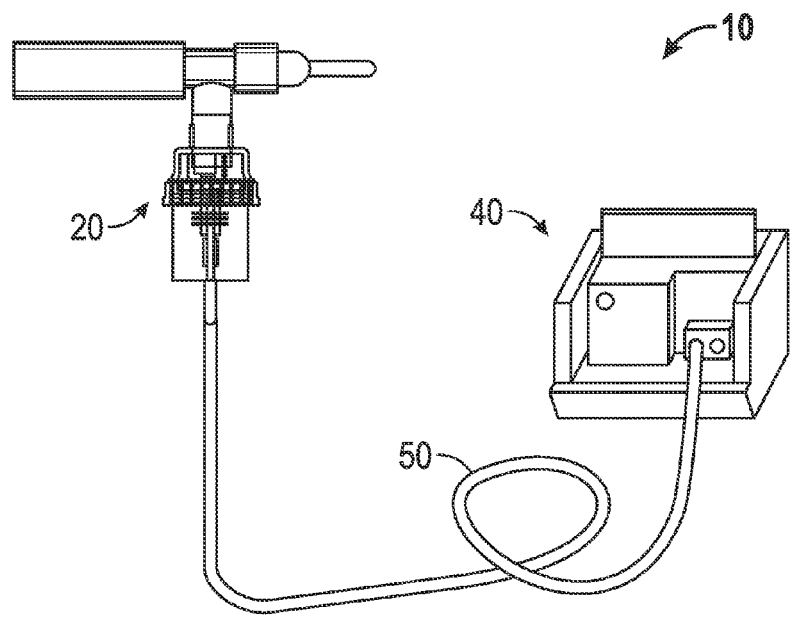
Figure 1B:
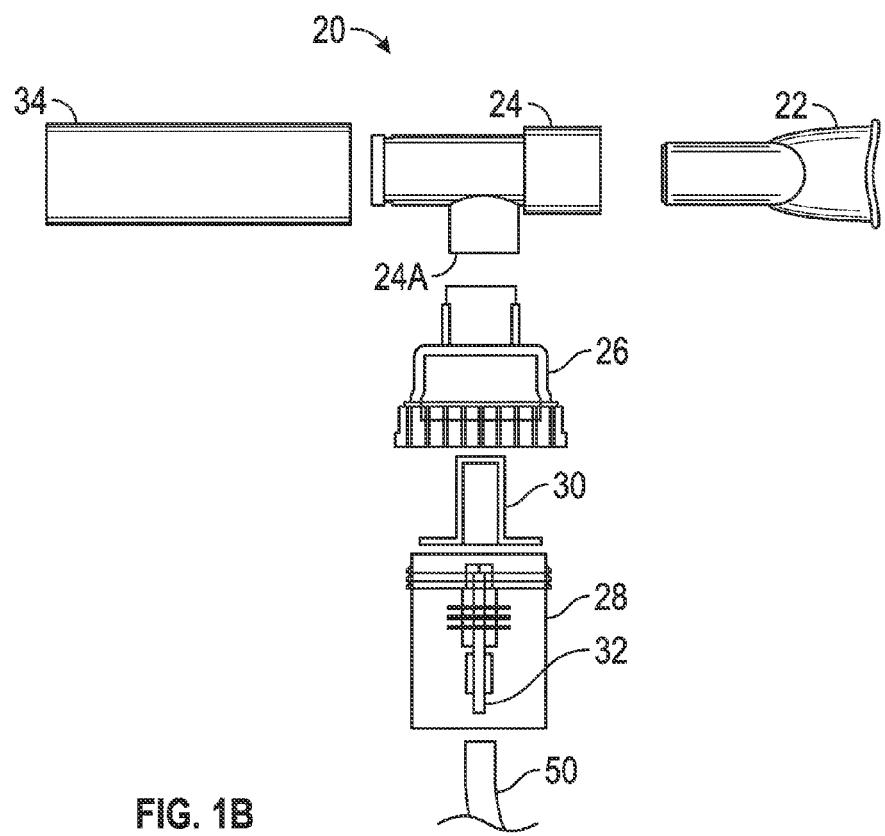
Figure 2:
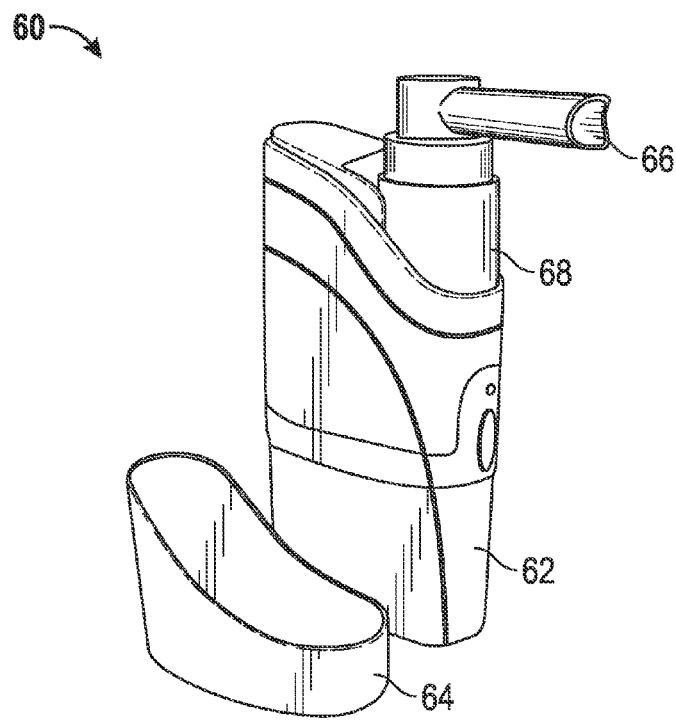
Figure 3:
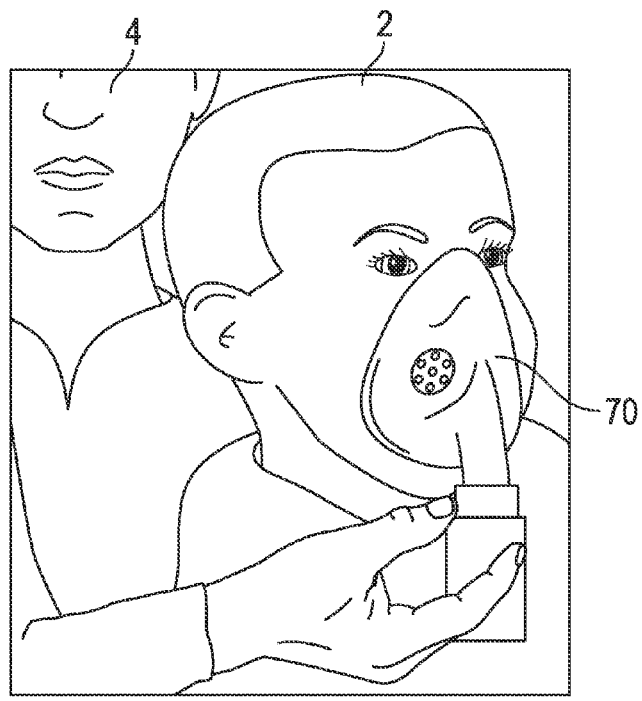
Figure 4:
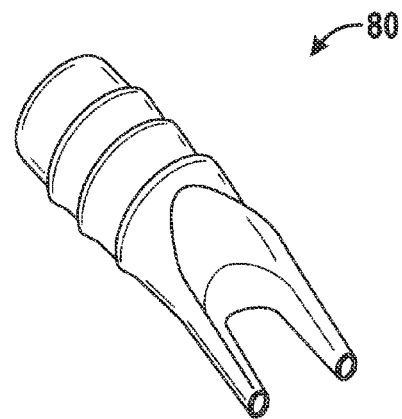

Nebulizers are available in various sizes, including tabletop units that are plugged into an electrical outlet, such as shown in FIG. 1A, and hand-held nebulizers, such as shown in FIG. 2 that run on batteries or can be plugged into a car's cigarette lighter. The aerosol mist created by either type of nebulizer is delivered to the patient through either a mask, such as shown in FIG. 3, a nasal piece, such as shown in FIG. 4, or a mouthpiece that fits into the mouth, as shown in FIG. 1B. These various prior art arrangements will be discussed in greater detail below.

Conventional designs for nebulizer dispensers do not allow sufficient adjustment to enable proper placement of the breathing piece proximate to the patient's mouth, nose, or face, depending on the type of breathing piece, for varying patient positions. As a result, caregivers are forced to adjust the position of the patient so that they may use the nebulizer. This may result in wasted time and patient discomfort. Use of a nebulizer in other than the intended position and orientation may also result in sub-standard treatment due to medication lost because of a poor fit of the breathing piece to the patient or inadequate nebulizer operation due to the position of the nebulizer during treatment.

SUMMARY

A nebulizer dispenser that allows for adjustment in all three rotational axes of the position of the breathing piece relative to the body of the dispenser is disclosed herein.

In certain embodiments, a nebulizer dispenser is disclosed that includes a T-piece and a body sealingly coupled to the T-piece and configured to contain a liquid medication. The nebulizer also includes a breathing piece sealingly coupled to the T-piece and a ball-and-socket joint coupled between the T-piece and one of the breathing piece and the body. The ball-and-socket joint is configured to allow rotational motion of the T-piece with respect to the one of the breathing piece and the body in a pitch axis, a yaw axis, and a roll axis.

In certain embodiments, a nebulizer dispenser is disclosed that includes a T-piece, a body sealingly coupled to the T-piece and configured to contain a liquid medication, and a breathing piece sealingly coupled to the T-piece. The nebulizer also includes a plurality of joints between the T-piece and at least one of the breathing piece and the body. Each of the plurality of joints is configured to allow rotational motion of the T-piece with respect to the one of the breathing piece and the body in at least one of a pitch axis, a yaw axis, and a roll axis of the breathing piece with respect to the body. The plurality of joints collectively allows rotational motion of the breathing piece with respect to the body in all of the pitch axis, the yaw axis, and the roll axis.

In certain embodiments, a nebulizer dispenser is disclosed that includes a T-piece comprising a breathing piece, a ball, and a first flow path passing from the ball to the breathing piece. The nebulizer also includes an intermediate piece having a socket configured to sealing mate with the ball of the T-piece and allow rotational motion of the T-piece with respect to the intermediate piece in a pitch axis, a yaw axis, and a roll axis. The intermediate piece has a first slip joint element with a second flow path passing from the first slip joint element to the socket. The nebulizer also includes a body having a second slip joint element configured to sealingly mate with the first slip joint element of the intermediate piece, an inlet configured to accept a flow of pressurized gas, and a nebulizer configured to contain a liquid medication and aerosolize the liquid medication into the accepted flow of pressurized gas and provide the mixture of pressurized gas and aerosolized medication though the second slip joint element, the intermediate piece, and the T-piece to the breathing piece.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 1A-1B depict a prior art nebulizer system with a dispenser and a separate source of pressurized air.

FIG. 2 depicts a prior art handheld nebulizer system.

FIG. 3 depicts a prior art mask used with a nebulizer in place of a mouthpiece.

FIG. 4 depicts a prior art nasal piece that may be used with a nebulizer in place of a mouthpiece.

FIGS. 5A-5B illustrate an exemplary embodiment of an adjustable nebulizer dispenser according to certain embodiments of the present disclosure.

FIGS. 6A-6B illustrate certain aspects of an adjustable nebulizer dispenser according to certain embodiments of the present disclosure.

FIG. 7 illustrates another embodiment of an adjustable nebulizer dispenser according to certain embodiments of the present disclosure.

FIGS. 8A-8D illustrate another embodiment of an adjustable nebulizer dispenser according to certain embodiments of the present disclosure.

FIGS. 9A-9E illustrate another embodiment of an adjustable nebulizer dispenser according to certain embodiments of the present disclosure.

DETAILED DESCRIPTION

A nebulizer dispenser that allows for adjustment in all three rotational axes of the position of the breathing piece relative to the body of the dispenser is disclosed herein.

Tabletop nebulizers and handheld nebulizers have dispensers that are conventionally held proximate to the patient's face to administer the aerosolized medication. While this disclosure discusses the various embodiments in terms of a handheld nebulizer, those of skill in the art will recognize that the concepts may also be applied to the dispenser portion of a main nebulizer without departing from the scope of this disclosure. Likewise, the breathing piece of a nebulizer may include a mouthpiece, a nasal piece, or a mask as illustrated in FIGS. 1B, 3, and 4. While this disclosure discusses the various embodiments in terms of a mouthpiece, those of skill in the art will recognize that the concepts may also be applied to other types of breathing pieces without departing from the scope of this disclosure.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

FIGS. 1A-1B depict a conventional nebulizer system 10 with a dispenser 20 and a separate source 40 of pressurized air. The source 40 provides pressurized air through tubing 50 to the dispenser 20. The source 40 typically includes an air compressor (not visible in FIG. 1A) that compresses ambient air to provide the pressurized air. In a healthcare facility, the pressurized air may be available from a wall fixture (not shown in FIG. 1) and, in this situation, the tubing 50 may be connected to the wall fixture rather than the source 40. Nebulizers may also operate using other gases in place of pure air, for example commercially pure oxygen as typically provided in a healthcare facility, oxygen-enriched air, a helium-oxygen mixture such as heliox, or any other mixture of gases suitable for breathing.

FIG. 1B is an exploded view of the dispenser 20 showing a T-piece 24 to which is connected a mouthpiece 22 and an exhalation tube 34. The T-piece 24 is connected through a neck 24A to a cap 26 that attaches to the nebulizer chamber 28, also referred to as a "medicine cup." The tubing 50 connects to an inlet 32 and the pressurized air entering through the tubing 50 entrains liquid medicine from the chamber 28 and disperses the entrained liquid medication as fine droplets and carries the droplets past an internal baffle 30 and through the T-piece 24 and mouthpiece 22 to the patient. The cap 26 may include valving (not visible in FIG. 1B) that prevents backflow of air into the nebulizer chamber 28 such that a patient's exhalation passes through the T-piece 24 and out the exhaust tube 34 that may contain a second set of valving (not visible in FIG. 1B) that prevents an inflow of air into the T-piece 24 such that the patient receives only medication-laden air from the nebulizer chamber 28 when the patient inhales.

FIG. 2 depicts a conventional handheld nebulizer 60. The nebulizer 60 has a medication chamber 68 that contains the liquid medicine and a mouthpiece 66 similar to the dispenser 20 of FIG. 1B. The hand-held nebulizer 60 includes a module 62 attached to the medication chamber 68, wherein the module includes a battery-powered air pump to take in ambient air and compress it to provide a stream of air and an aerosolizer to convert the liquid medicine to an aerosol. A typical nebulizer 60 also includes a cap 64 to protect the mouthpiece 66. A handheld nebulizer 60 comprises a self-contained system for aerosolizing a liquid medication into a stream of air provided through the breathing piece to the patient.

FIG. 3 depicts a mask 70 used with a nebulizer 10, 60 in place of a mouthpiece 22, 66. It is easier for certain patients 2, such as an infant, to use a mask that allows the caregiver 4 to administer the medication without the patient 2 having to actively use a mouthpiece 22, 66.

FIG. 4 depicts a nasal piece 80 that may be used with a nebulizer 10, 60 in place of a mouthpiece 22, 66 for certain treatments or medications. This type of breathing piece is particularly adapted for delivering aerosolized medication to the nasal sinuses and passages.

Figure 5A:
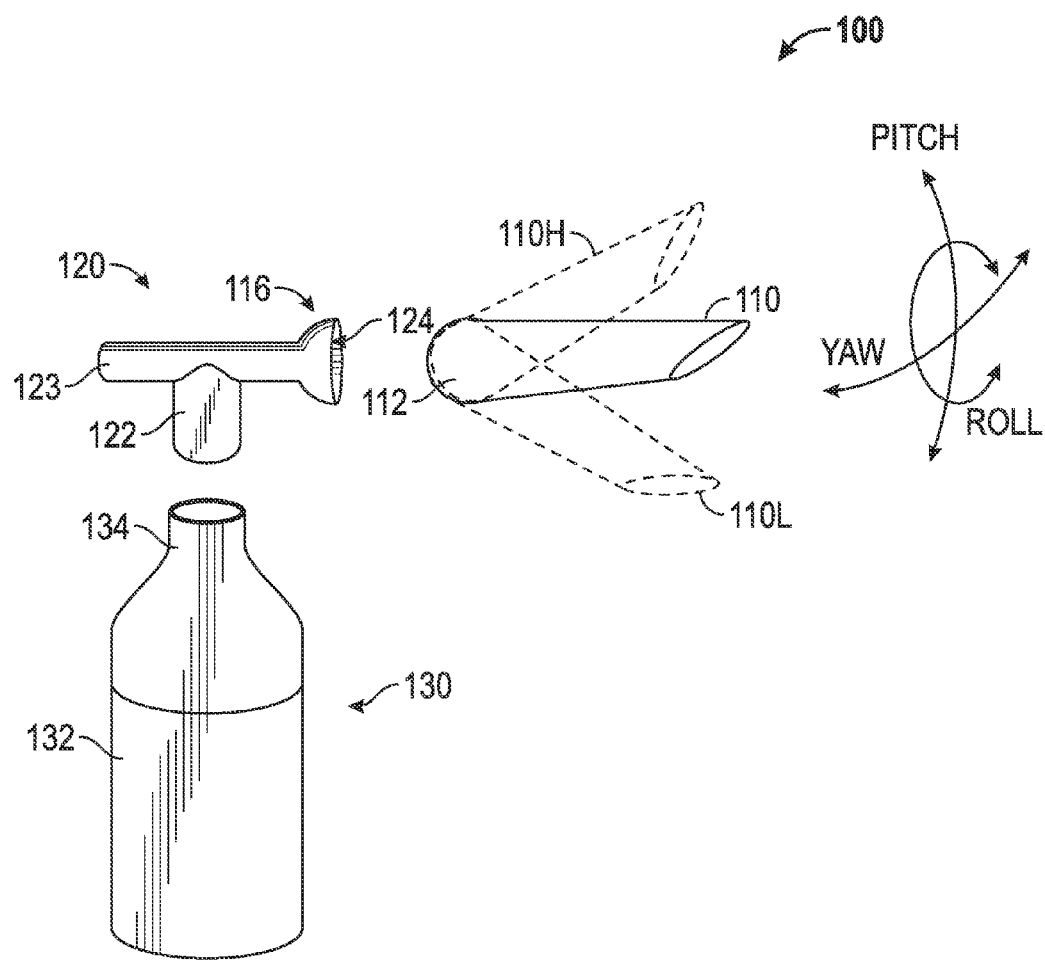
Figure 5B:
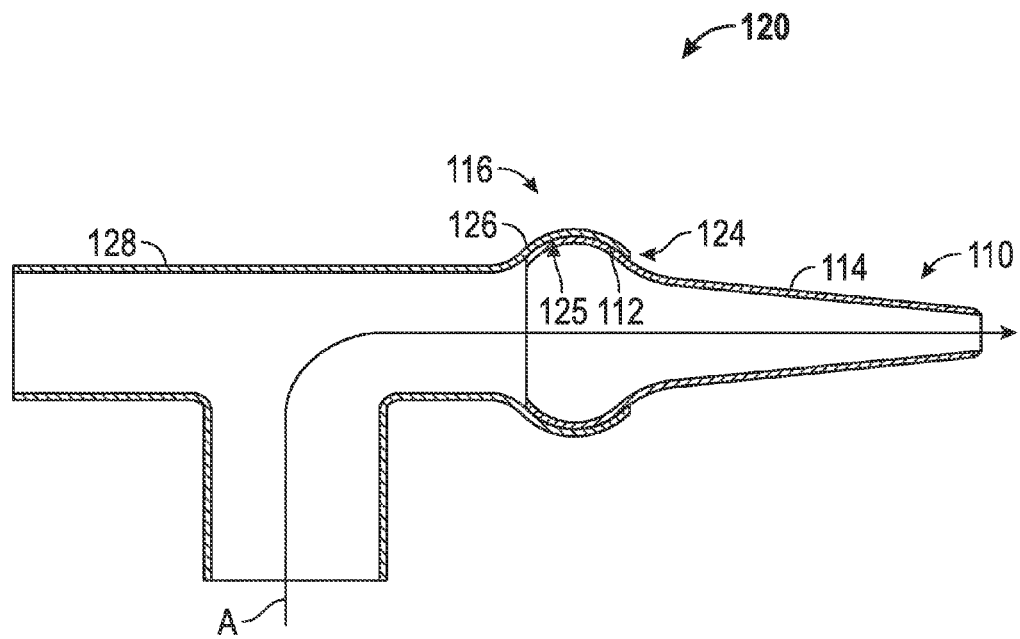

FIGS. 5A-5B illustrate an exemplary embodiment 100 of an adjustable nebulizer dispenser according to certain embodiments of the present disclosure. In this embodiment 100, a mouthpiece 110 is coupled to a T-piece 120 via a ball-and-socket joint 116 comprising a ball 112 formed at one end of the mouthpiece 110 and a socket 124 formed at one end of the T-piece 120. The ball-and-socket joint 116 allow the mouthpiece 110 to move simultaneously in the rotational axes of pitch, yaw, and roll as indicated by the arrows in FIG. 5A by rotational movement of the ball 112 within the socket 124. Representative positions of the rotated mouthpiece 110 are shown as dashed outlines 110H and 110L, although this is exemplary only, as the ball-and-socket joint 116 allows the mouthpiece 110 to be moved to a number of positions. The T-piece 120 is coupled to a handheld dispenser body 130 via a neck 122 that couples to a neck 134 of the dispenser body 130. In this embodiment, the dispenser body 130 comprises a medication chamber 132 as well as an aerosolizer, a power source, and a control element (not visible in FIG. 5A) such as a switch that activates the aerosolizer.

In certain embodiments, a ball 112 may be formed at one end of the T-piece 120 and the socket 124 formed at one end of the mouthpiece 110. In certain embodiments, the T-piece 120 may be configured such that the socket 124 is position on a top of the T-piece 120, or on a side of the T-piece 120, or at a different nominal angle, or with the exhaust connection port 123 arranged at a different location or at a different angle. In certain embodiments, the T-piece 120 may not resemble a "T" and may be formed in any of a variety of configurations that provide the function of interconnecting the dispenser body 130 with a mouthpiece 110, mask 70, nasal piece 80, or other respiratory interface device.

FIG. 5B is a cross-section of the T-piece 120 and mouthpiece 110 of FIG. 5A showing the ball-and-socket joint 116. The ball 112 is generally formed as a partial sphere coupled to one end of a tapered portion 114 that is shaped at the other end to be comfortably accepted in a patient's mouth. In certain embodiments, the ball 112 or similar connector may be formed as part of a mask similar to the mask 70 of FIG. 3, or formed as part of a nasal piece similar to the nasal piece 80 of FIG. 4. The socket 124 comprises at least one wall 126 having an interior surface 125 that is generally formed as a partial spherical cavity coupled to one end of a body 128 of the T-piece 120. In certain embodiments, the ball 112 may be coupled to the T-piece body 128 and the socket formed at one end of the tapered portion 114 of the mouthpiece 110. The T-piece 120 and mouthpiece 110 are hollow and allow air to flow as indicated by the arrow labeled "A." In certain embodiments, the ball-and-socket joint 116 is configured such that the ball 112 will remain in any orientation with respect to the socket 124 once moved to that orientation by a user.

In certain embodiments, the mouthpiece 110 may be removed from the T-piece 120, for example to wash or sterilize one or both of the mouthpiece 110 and the T-piece 120, and reinserted for re-use. In certain embodiments, removal of the mouthpiece 110 may render the mouthpiece unsuitable for re-use, for example by damage to the ball 112.

In certain embodiments, the ball 112 may comprise a resilient material. In certain embodiments, the resilient material may comprise a plastic such as polypropylene, polyethylene, and polytetrafluoroethylene (PTFE). In certain embodiments, the ball 112 may comprise a flexible material. In certain embodiments, the ball 112 may comprise a rigid material. In certain embodiments, the rigid material may comprise a plastic such as acrylic, polycarbonate, and polyether ether ketone (PEEK). In certain embodiments, the flexible material or the rigid material may comprise a metal, for example aluminum, copper, and nickel, or an alloy of metals, such as stainless steel and beryllium-copper.

Figure 6A:
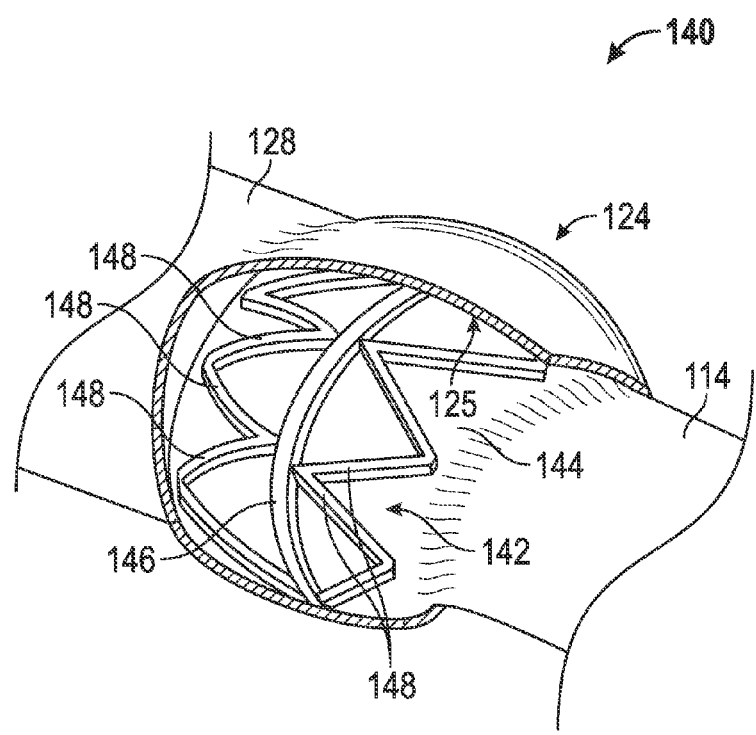
Figure 6B:
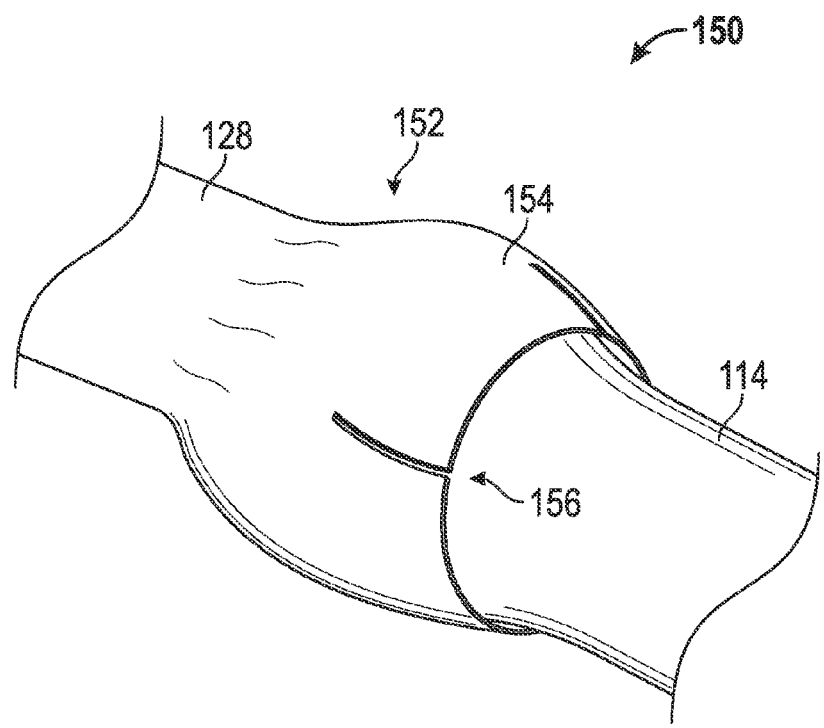

FIGS. 6A-6B illustrate certain aspects of a ball-and-socket joint 140, 150 according to certain embodiments of the present disclosure. In the embodiment 140 shown in FIG. 6A, the surface 144 of the ball 142 may comprise ribs 148 or similar raised elements that provide portions of its spherical surface 144, with reliefs or notches between these ribs 148 so as to reduce the friction between the ball 142 and the socket 124. In certain embodiments, a portion of the ribs or similar raised elements may be discontinuous, for example as a raised post (not shown in FIG. 6A). In certain embodiments, there is a continuous circumferential ridge 146 that encircles a portion of the ball 142 and configured such that the ridge 146 is in continuous contact with the interior surface 125 of the socket 124 over the entire range of motion of the ball 142 with respect to the socket 124, thereby providing a sealing surface between the ball 142 and the socket 124. In certain embodiments, the ridge 146 is offset from a midline of the ball 142. In certain embodiments, the surface 144 of the ball 142 may be smooth and the ribs 148 or similar raised elements may be formed in the surface 125 of the socket 124, with reliefs or notches between these ribs so as to reduce the friction between the ball 142 and the interior surface 125 of the socket 124. In certain embodiments, the ridge 146 may be formed in the surface 125 and configured such that the ridge 146 is in continuous contact with the surface 144 over the entire range of motion of the ball 142 with respect to the socket 124, thereby providing a sealing surface between the ball 142 and the socket 124.

FIG. 6B depicts an embodiment of a ball-and-socket joint 150 that has a socket 152 formed by a wall 154 having one or more slits 156 arranged so as to allow portions of the wall 154 to flex outward, for example to accept insertion of a new mouthpiece 110, and then return toward the original position. In certain embodiments, the slits 156 are aligned with an axis of symmetry of the socket 152. In certain embodiments, the wall 154 may comprise a resilient material. In certain embodiments, the resilient material may comprise a plastic such as polypropylene, polyethylene, and polytetrafluoroethylene (PTFE). In certain embodiments, the wall 154 may comprise a flexible material. In certain embodiments, the wall 154 may comprise a rigid material. In certain embodiments, the flexible material or the rigid material may comprise a metal, for example aluminum, copper, and nickel, or an alloy of metals, such as stainless steel and beryllium-copper. In certain embodiments, the rigid material may comprise a plastic such as acrylic, polycarbonate, and polyether ether ketone (PEEK).

In certain embodiments, the dispenser 100 may provide a plurality of adjustment points, or joints, each providing angular motion in one or more axes between adjacent elements such that the mouthpiece 110 is adjustable in all three of the pitch, yaw, and roll axes of FIG. 5A with respect to the dispenser body 130. In certain embodiments, one or more of the plurality of joints may allow angular motion in an axis by flexing rather than a sliding displacement of a first element with respect to a second element. Example embodiments with such features are provided below, but one of skill in the art will recognize that the same features can be combined, without departing from the scope of this disclosure, to create additional configurations so as to collectively provide three-axis flexibility between the mouthpiece 100 and the dispenser body 130.

Figure 7:
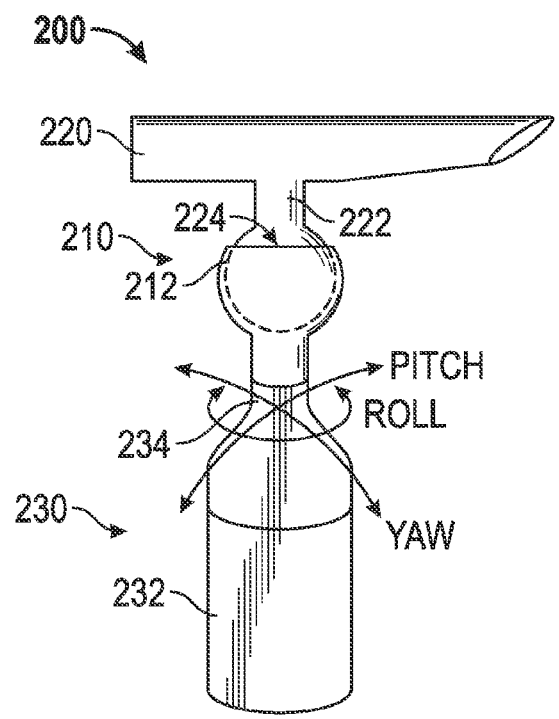

FIG. 7 illustrates another embodiment 200 of an adjustable nebulizer dispenser according to certain embodiments of the present disclosure. A ball-and-socket joint 210, for example one similar to the ball-and-socket joint 116 shown in FIG. 5B, is formed between the neck 222 of a T-piece 220 and a neck 234 of a dispenser body 230. The ball-and-socket joint 210 comprises a ball 212 that is generally formed as a partial sphere coupled to the neck 222 of the T-piece 220 and a socket 224 that is coupled to the neck 234 of the dispenser body 230. The ball-and-socket joint 210 may comprise features from one or more of the previously described ball-and-socket joints 116, 140, 150 and provide motion in the three axes of pitch, yaw, and roll as indicated in FIG. 7. The dispenser body 230 may comprise one or more of a medication chamber, an aerosolizer, a power source, and a control element (not visible in FIG. 7).

In certain embodiments, the ball-and-socket joint 210 may be configured such that the ball 212 is coupled to the neck 234 of the dispenser body 230 and the socket 224 is formed at one end of the neck 222 of the T-piece 220.

Figure 8A:
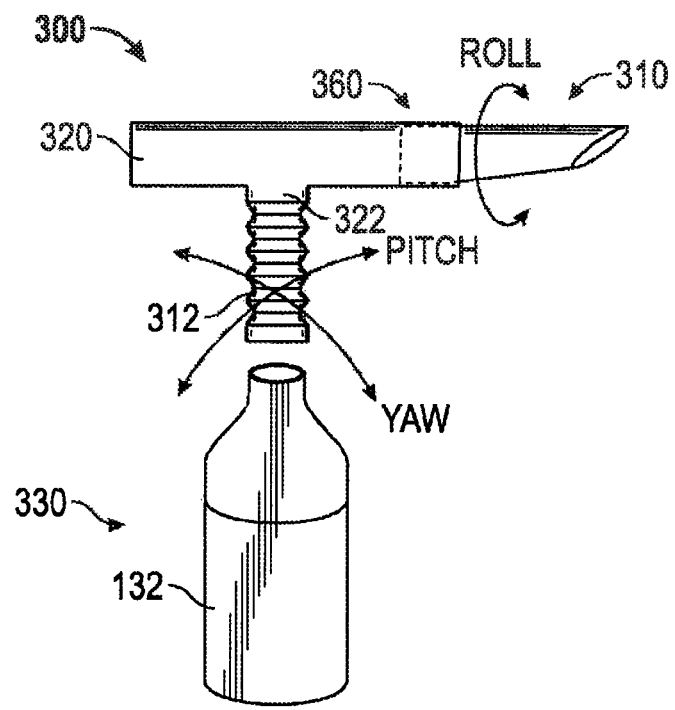

FIGS. 8A-8D illustrate another embodiment 300 of an adjustable nebulizer dispenser according to certain embodiments of the present disclosure. As shown in FIG. 8A, the neck 322 comprises a flexible joint 312 that bends to allow motion of the T-piece 320 with respect to the dispenser body 330 in the pitch and yaw axes but does not provide for rotation about an axis perpendicular to the pitch and yaw axes shown in FIG. 8A. In certain embodiments, the flexible joint 312 comprises a plurality of corrugations, which are described in greater detail with respect to FIGS. 8B and 8C. This embodiment 300 also comprises a rotational joint 360 between the T-piece 320 and the mouthpiece 310 that allows rotation of the mouthpiece 310 in a roll axis with respect to the T-piece 320 as shown in FIG. 8A. The rotational joint 360 is described in greater detail with respect to FIG. 8D. In certain embodiments, the rotational joint 360 and the flexible joint 312 are interchanged such that the flexible joint 312 is sealingly disposed between the T-piece 320 and the mouthpiece 310 and the rotational joint 360 is sealingly disposed between the T-piece 320 and the dispenser body 330. In certain embodiments, the flexible joint 312 and the rotational joint 360 are both disposed between the T-piece 320 and the same one of the mouthpiece 310 and the body 330.

Figure 8B:
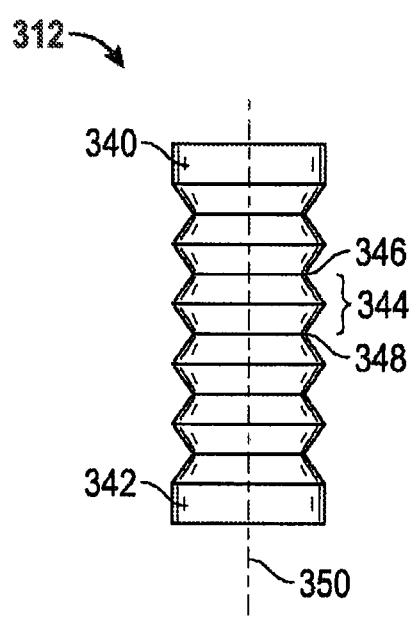

FIG. 8B depicts an example embodiment of the flexible joint 312 in an undeformed position, i.e. with the tube top 340 and tube bottom 342 parallel and aligned perpendicular to a common axis 350. The flexible joint 312 is, in this example, axially symmetric about axis 350 and comprises a plurality of corrugations 344 each comprising a pair of sharp-edged conical sections. In certain embodiments, the corrugations 344 may have other profiles and may have radiused concave or convex edges. In certain embodiments, each corrugation may have a first stable configuration as shown in FIG. 8B, wherein the respective top 346 and bottom 348 are parallel and aligned perpendicular to a common axis, for example axis 350.

Figure 8C:
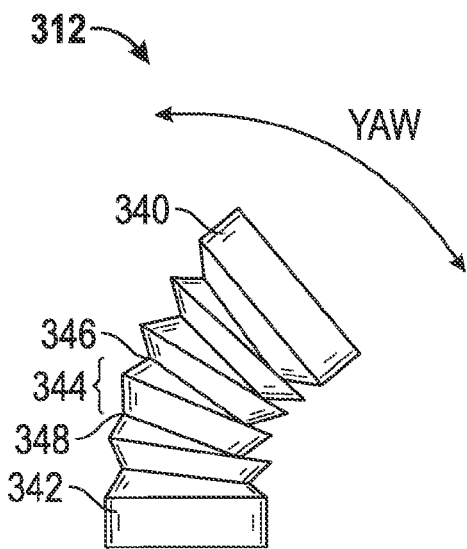

FIG. 8C depicts the flexible joint 312 in a deformed position, i.e. with the tube top 340 and bottom tube 342 positioned at an angle to each other. In certain embodiments, each corrugation 344 may have a second stable position, for example as shown in FIG. 8B, where the top 346 is positioned at an angle to the bottom 348. In certain embodiments, a user may reposition the tube top 340 with respect to the tube bottom 342, thereby causing one or more of the corrugations 344 to move between the first stable position of FIG. 8B and the second stable position of FIG. 8C. In certain embodiments, each corrugation 344 will remain in the first or second stable position once moved to that position by a user. In certain embodiments, the corrugations 344 are configured such that each corrugation 344 will snap between the respective first and second stable positions without a stable intermediate position.

Figure 8D:
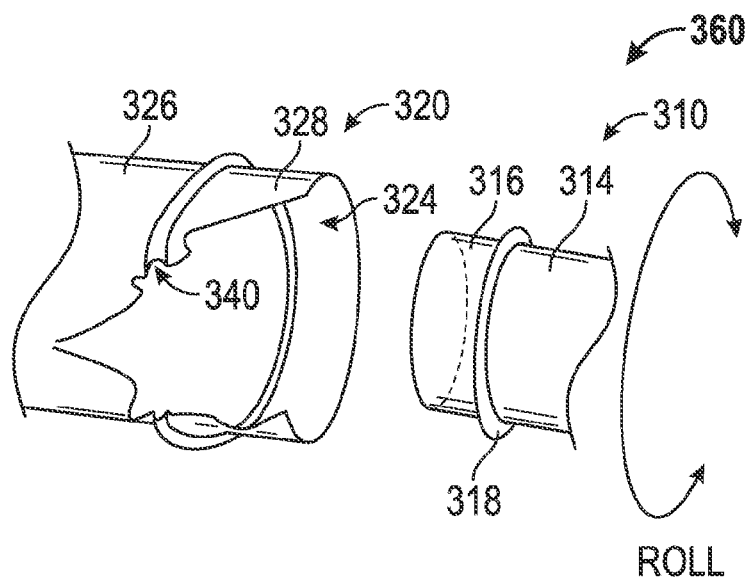

FIG. 8D is a partial cutaway view of an exemplary embodiment of a rotational joint 360. The rotational joint 360 comprises an inner cylinder 316 that is coupled to one end of a tapered portion 314 that is otherwise similar to the tapered portion 114 of FIG. 5B, and an outer cylinder 328 that is coupled to one end of a body 326 of the T-piece 320. The outer cylinder 328 comprises an interior cavity 324 that is sized and configured to accept the inner cylinder 316. In certain embodiments, the outer cylinder 328 comprises a circumferential groove 340 and the inner cylinder 316 comprises a circumferential ridge 318 sized and positioned such the ridge 318 engages the groove 340 when the inner cylinder 316 is properly located in the cavity 324, so as to retain the mouthpiece 310 in the T-piece 320. In certain embodiments, the outer cylinder 328 comprises a flexible material such that the outer cylinder 328 temporarily deforms as the inner cylinder 316 is introduced into the cavity 324 such that the ridge 318 can reach the groove 340. In certain embodiments, the ridge 318 and the groove 340 form a rotatable seal with respect to the cavity 324.

In certain embodiments, the outer cylinder 328 comprises a raised element (not shown in FIG. 8D) extending inward from the surface of the cavity 324 and the inner cylinder 316 comprises a groove (not shown in FIG. 8D) configured to engage the raised element when the inner cylinder 316 is disposed within the cavity 324. In certain embodiments, the raised element is configured to engage the groove, for example a maximum diameter of the raised element being slightly larger than a maximum diameter of the groove, so as to form a seal between the inner cylinder 316 and the outer cylinder 328.

In certain embodiments, the inner and outer cylinders 316, 328 comprise separate retention means and sealing means. In certain embodiments, the mouthpiece 310 is retained in the cavity 324 by a post (not shown in FIG. 8D) extending from the surface of the inner cylinder 316 and disposed such that the post engages groove 340. In certain embodiments, a second ridge (not shown in FIG. 8D) extends outward from the surface of the inner cylinder 316 and engages the interior surface of cavity 324 to form a seal. It will be apparent to those of skill in the art of other means to rotatably couple a pair of nested cylinders 316, 328 as well as other means to provide a rotatable seal between the nested cylinders 316, 328.

In certain embodiments, one or both of the inner and outer cylinders 316, 328 may comprise a flexible material. In certain embodiments, the resilient material may comprise a plastic such as polypropylene, polyethylene, and polytetrafluoroethylene (PTFE). In certain embodiments, one or both of the inner and outer cylinders 316, 328 may comprise a flexible material. In certain embodiments, one or both of the inner and outer cylinders 316, 328 may comprise a rigid material. In certain embodiments, the flexible material or the rigid material may comprise a metal, for example aluminum, copper, and nickel, or an alloy of metals, such as stainless steel and beryllium-copper. In certain embodiments, the rigid material may comprise a plastic such as acrylic, polycarbonate, and polyether ether ketone (PEEK).

Figure 9A:
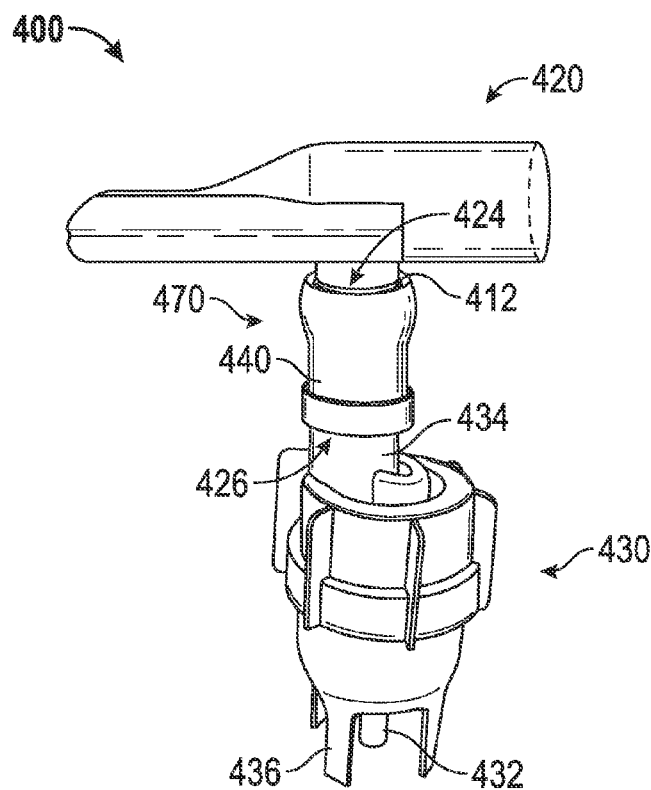

FIGS. 9A-9E illustrate another embodiment of an adjustable nebulizer dispenser 400 according to certain embodiments of the present disclosure. FIG. 9A depicts an assembled dispenser 400, comprising a T-piece 420 that includes a ball 412 that is seated in a socket 424 formed in a top end of an intermediate piece 440, thereby forming a ball-and-socket joint 470. The intermediate piece 440 has a slip socket 426 at a bottom end, with slip socket 426 mated with a neck 434 of the nebulizer body 430. In this example, the nebulizer 400 is configured to receive a compressed gas at inlet 432 from an external source (not shown in FIG. 9A). The body 430 includes legs 436 arranged so as to allow that nebulizer 400 to be placed on a surface, such as a tabletop, without the inlet 432 coming into contact with the surface so as to avoid contamination.

Figure 9B:
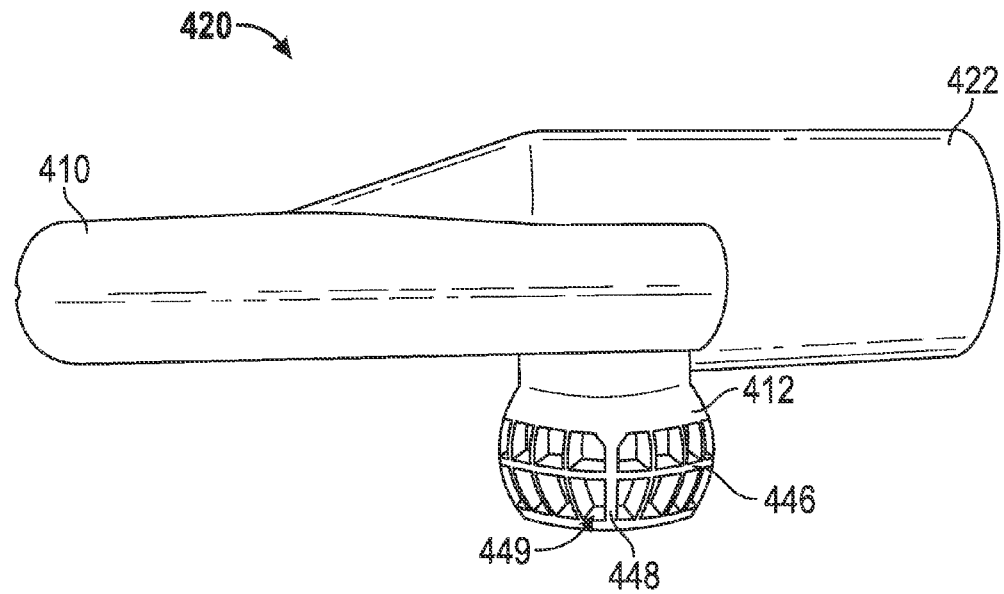
Figure 9C:
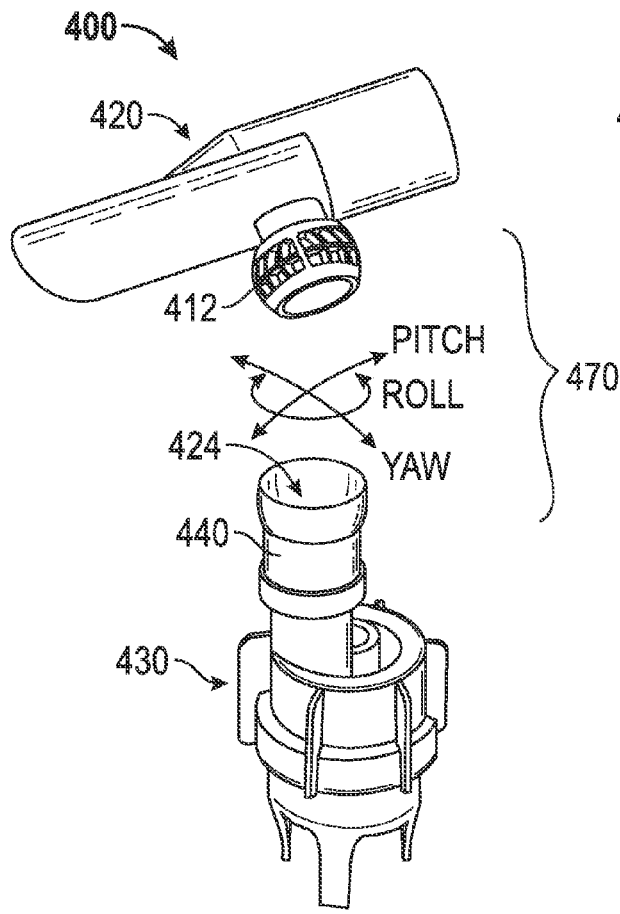

FIG. 9B depicts the T-piece 420. This example embodiment has a breathing piece 410 and an exhaust tube 422 integrally molded as part of the T-piece 420. The ball 412 includes a circumferential ridge 446 and a plurality of ribs 448 whose exterior surfaces are coincident with a spherical surface, with recesses 449 formed between the ridge 446 and ribs 448. The ball 412 may include a center bore (not visible in FIG. 9B) having a smooth interior surface. When mated with a socket (not shown in FIG. 9B) having a smooth spherical interior surface, the ridge 446 and ribs 448 will provide a seal while reducing the friction between the T-piece 420 and the socket, while the recesses 449 reduce the amount of material required to form the T-piece 420.

It is only necessary that a portion of the ball 412 contact the socket 424 to provide a seal. In certain embodiments, a portion of the ball 412, for example the tops of the ridge 446 and the ribs 448, may be coincident with a first virtual spherical interface. Similarly, a portion of an interior surface of a socket, such as the socket 424 of FIG. 9A, may be coincident with a second virtual surface. In certain embodiments, the first and second virtual spherical interfaces may be coincident such that, when the ball 412 is disposed within the socket 424, the portion of the ball 412 and the portion of the socket 424 may be in contact. In certain embodiments, the second virtual spherical interface may be slightly smaller than the first virtual spherical interface such that the walls of the socket 424 must be expanded, e.g. an interference fit, when the ball 412 is disposed within the socket 424, sufficient that the portion of the interior surface of the socket 424 is coincident with the first virtual surface of the ball 412.

It will be apparent to those of skill in the art that the T-piece 420 may be formed in other ways, for example by molding one or both of the breathing piece 410 and the exhaust tube 422 as separate pieces and either bonding them to a centerpiece to form the T-piece 420 or separably attaching one or both of the breathing piece 410 and the exhaust tube 422, for example with a slip joint having an interference fit. Likewise, the intermediate piece 440 may be formed as an integral part of the nebulizer body 430 or formed separately and then bonded to the nebulizer body 430 to form an integral assembly. The various features and aspects disclosed herein may be provided as separate elements or integrated in various combinations without departing from the scope of this disclosure.

FIG. 9C depicts the T-piece 420 of the dispenser 400 separated from the intermediate piece 440, for example prior to mating the ball 412 with the socket 424. In this example, the walls of the socket 424 may be formed of a partially transparent material, such as a polycarbonate, for example to assist in verifying the cleanliness of the intermediate piece 440 after washing. In this example, the walls of the socket 424 may be formed of a resilient plastic, such as a polyethylene, for example to enable the walls of the socket 424 to stretch while accepting or releasing the ball 412 and then return toward the original shape so as to retain the ball 412 in contact with the interior surface of the socket 424, thereby forming the ball-and-socket joint 470. It can be seen how the spherical interface between the ball 412 and socket 424 allows motion in all of the pitch, yaw, and roll axes.

Figure 9D:
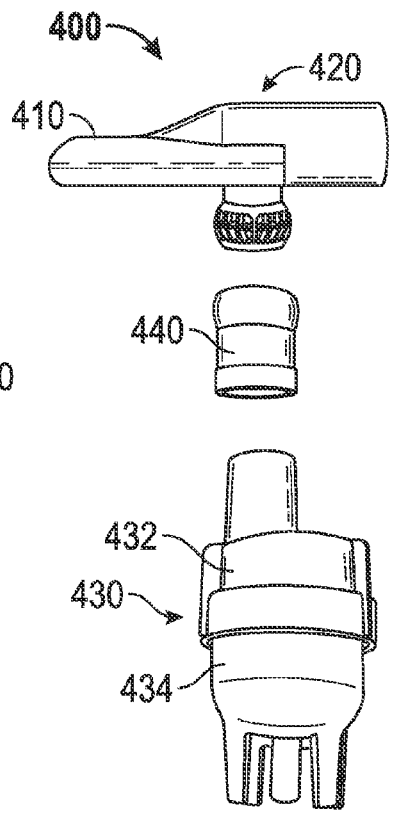

FIG. 9D is an exploded view of this example embodiment of a nebulizer 400. The ability to separate the nebulizer 400 into these separate components may improve the ability to wash and disinfect the interior surface of one or more of the T-piece 420, the intermediate piece 440, and the body 430. In certain embodiments, one or more of these components may be further separable, for example the body 430 may allow the cap 432 to be separated from the nebulizer chamber 434, or a breathing piece 410 may be separable from a body of the T-piece 420.

Figure 9E:
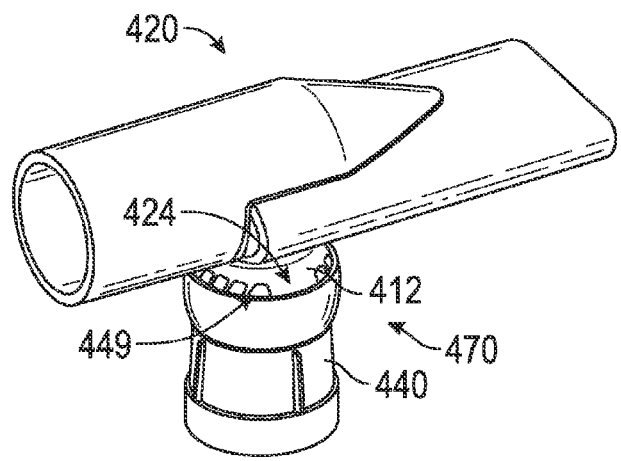

FIG. 9E is a perspective view of the ball-and-socket joint 470 between the T-piece 420 and the intermediate piece 440. It can be seen that a portion of the recesses 449 are exposed in this orientation of the ball 412 within the socket 424. A seal between the ball 412 and socket 424 is maintained, in this example, by the ridge 446 (not visible in FIG. 9E) in contact with the interior surface of the socket 424.

It can be seen that the disclosed embodiments of the nebulizer dispenser provide motion of the breathing piece relative to the dispenser body so as to enable patients to use the dispenser while in a wider range of positions and with greater comfort. In certain embodiments, a ball-and-socket joint allows rotational motion in pitch, yaw, and roll axes. In other embodiments, multiple joints are provided, wherein each joint allows rotational motion in one or more of the pitch, yaw, and roll axes such that the combination of the multiple joints allows rotational motion in all of the pitch, yaw, and roll axes.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A nebulizer dispenser comprising:
   a T-piece;
   a body sealingly coupled to the T-piece, the body configured to contain a liquid medication;
   a breathing piece sealingly coupled to the T-piece; and
   a ball-and-socket joint coupled between the T-piece and one of the breathing piece and the body, the ball-and-socket joint configured to allow rotational motion of the T-piece with respect to the one of the breathing piece and the body in a pitch axis, a yaw axis, and a roll axis, wherein the ball-and-socket joint comprises a ball and a socket, the ball having (i) a first circumferential ridge, a second circumferential ridge, and a plurality of ribs transverse to the first and second ridges, the first ridge and the ribs having top surfaces forming a common spherical surface, and (ii) a recessed surface defined by the first and second ridges and the ribs, the recessed surface recessed from the spherical surface, wherein the top surfaces of the first ridge and the ribs are configured to engage an inner surface of the socket so as to form a seal to restrict fluid flow between the ball and the socket, wherein a top surface of the second ridge is raised above the recessed surface and coincident with the spherical surface.

2. The dispenser of claim 1, wherein the ball-and-socket joint is configured such that the ball will remain in a selected orientation with respect to the socket once moved to that orientation by a user.

3. The dispenser of claim 1, wherein:
the ball is coupled to one of the T-piece and the breathing piece; and
the socket is formed in the other of the T-piece and the breathing piece.

4. The dispenser of claim 1, wherein the breathing piece is formed as an integral part of the T-piece.

5. The dispenser of claim 1, wherein:
the ball is coupled to one of the T-piece and the body; and
the socket is coupled to the other of the T-piece and the body.

6. The dispenser of claim 5, wherein the socket is formed as an integral part of one of the T-piece and the body.

7. The dispenser of claim 5, further comprising an intermediate piece sealingly coupled between the T-piece and the body, wherein:
one of the ball and the socket is formed at one end of the intermediate piece; and
the other end of the intermediate piece is sealingly coupled to the body of the nebulizer dispenser.

8. The dispenser of claim 1, wherein the socket comprises a smooth interior spherical surface and the top surfaces are configured to continuously engage the inner surface of the socket over a range of pitch, yaw, and roll motion of the T-piece with respect to the one of the breathing piece and the body so as to form the seal between the ball and the socket.

9. The dispenser of claim 1, wherein the dispenser is configured to accept a flow of gas into the body, aerosolize the liquid medication into the flow of gas, and provide the flow of gas through the breathing piece to a patient.

10. The dispenser of claim 9, wherein the dispenser is a self-contained system that comprises:
a pump configured to draw in ambient air, compress the air, and provide the flow of air into the body;
an aerosolizer configured to generate droplets from the liquid medicine that is contained in the body; and
a power source coupled to the pump.

11. The dispenser of claim 9, wherein the dispenser is configured to accept a flow of pressurized gas from an external source.

12. The dispenser of claim 11, wherein the gas comprises one or more of ambient air, oxygen-enriched air, commercially pure oxygen, and a mixture comprising oxygen and helium.

13. The dispenser of claim 1, wherein the breathing piece comprises a mouthpiece.

14. The dispenser of claim 1, wherein the breathing piece comprises a nasal piece.

15. The dispenser of claim 1, wherein the breathing piece comprises a mask.

16. The dispenser of claim 1, wherein at least one of the T-piece and the breathing piece comprises a resilient material.

17. A nebulizer dispenser comprising:
a T-piece comprising a breathing piece, a ball having (i) a first raised circumferential ridge, a second raised circumferential ridge, and a plurality of raised ribs transverse to the first and second ridges, the first ridge and the ribs have top surfaces forming a common spherical surface, and (ii) a recessed surface defined by the first and second ridges and the ribs, the recessed surface recessed from the spherical surface of the first and second ridges and the ribs, wherein a first flow path passes through a bore of the ball to the breathing piece;
an intermediate piece comprising:
a socket configured to mate with the ball of the T-piece and allow rotational motion of the T-piece with respect to the intermediate piece in a pitch axis, a yaw axis, and a roll axis, wherein the top surfaces of the first ridge and the ribs are configured to engage an inner surface of the socket so as to form a seal to restrict fluid flow between the ball and the socket, and wherein a top surface of the second ridge is raised above the recessed surface and coincident with the spherical surface;
a first slip joint element; and
a second flow path passing from the first slip joint element to the socket; and
a body comprising:
a second slip joint element configured to sealingly mate with the first slip joint element of the intermediate piece;
an inlet configured to accept a flow of pressurized gas; and
a nebulizer configured to contain a liquid medication and aerosolize the liquid medication into the accepted flow of pressurized gas and provide the mixture of pressurized gas and aerosolized medication though the second slip joint element, the intermediate piece, and the T-piece to the breathing piece.

18. The nebulizer dispenser of claim 17, wherein the intermediate piece and a portion of the body are formed as an integral piece.

19. The nebulizer dispenser of claim 17, wherein the breathing piece is formed as a separately formed first portion of the T-piece and removably coupled to a separately formed second portion of the T-piece to form the T-piece.

20. The nebulizer dispenser of claim 17, wherein the ball comprises a plurality of recesses.

* * * * *